United States Patent
Li et al.

(10) Patent No.: US 10,888,544 B2
(45) Date of Patent: Jan. 12, 2021

(54) METHODS FOR TREATING GAUCHER DISEASE

(71) Applicant: Genzyme Corporation, Cambridge, MA (US)

(72) Inventors: Jing Li, Bridgewater, NJ (US); M. Judith Peterschmitt, Watertown, MA (US); Vanaja Kanamaluru, Bridgewater, NJ (US); Jun Chen, Bridgewater, NJ (US); Sebastiaan J. M. Gaemers, Naarden (NL); Dan Rudin, Cambridge, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 16/219,064

(22) Filed: Dec. 13, 2018

(65) Prior Publication Data

US 2019/0183844 A1    Jun. 20, 2019

Related U.S. Application Data

(60) Provisional application No. 62/599,467, filed on Dec. 15, 2017.

(51) Int. Cl.

| | | |
|---|---|---|
| *A61K 31/343* | (2006.01) | |
| *A61K 31/496* | (2006.01) | |
| *A61K 31/15* | (2006.01) | |
| *A61K 45/06* | (2006.01) | |
| *A61K 31/138* | (2006.01) | |
| *A61K 31/427* | (2006.01) | |
| *A61P 3/00* | (2006.01) | |
| *A61K 31/4422* | (2006.01) | |
| *A61K 31/381* | (2006.01) | |
| *A61K 31/4025* | (2006.01) | |
| *A61P 1/16* | (2006.01) | |
| *A61P 13/12* | (2006.01) | |

(52) U.S. Cl.
CPC .......... *A61K 31/343* (2013.01); *A61K 31/138* (2013.01); *A61K 31/15* (2013.01); *A61K 31/381* (2013.01); *A61K 31/4025* (2013.01); *A61K 31/427* (2013.01); *A61K 31/4422* (2013.01); *A61K 31/496* (2013.01); *A61K 45/06* (2013.01); *A61P 1/16* (2018.01); *A61P 3/00* (2018.01); *A61P 13/12* (2018.01)

(58) Field of Classification Search
CPC .... A61K 31/343; A61K 31/496; A61K 31/15; A61K 45/06; A61K 31/138; A61K 31/427; A61K 31/4422; A61K 31/381; A61K 31/4025; A61K 2300/00; A61P 3/00; A61P 1/16; A61P 13/12; A61P 43/00

See application file for complete search history.

(56) References Cited

U.S. PATENT DOCUMENTS

| | | | |
|---|---|---|---|
| 6,051,598 A | 4/2000 | Shayman et al. | |
| 7,196,205 B2 | 3/2007 | Siegel et al. | |
| 2013/0137743 A1* | 5/2013 | Liu | A61K 31/4025 |
| | | | 514/422 |

FOREIGN PATENT DOCUMENTS

WO        2011066352 A1      6/2011

OTHER PUBLICATIONS

Li, J., et al., Impact of Hepatic and Renal Impairment on the Pharmacokinetics and Tolerability of Eliglustat, poster dated Feb. 2018, 1 page.
McElroy, S., et al., CYP2D6 Genotyping as an Alternative to Phenotyping for Determination of Metabolic Status in a Clinical Trial Setting, AAPS Pharmsci. 2000, 2(4), article 33, 11 pages.
NCT02536911, A Study of the Effects of Hepatic Impairment on the Pharmacokinetics and Tolerability of Eliglustat Tartrate, as retrieved from https://clinicaltrials.gov/ct2/show/NCT02536911 on Feb. 15, 2019, 8 pages.
NCT02536937, A Study of the Effects of Renal Impairment on the Pharmacokinetics and Tolerability of Eliglustat Tartrate as retrieved from https://clinicaltrials.gov/ct2/show/NCT02536937?term=NCT02536937&rank=1 on Feb. 15, 2019, 9 pages.
Belmatoug et al., Management and monitoring recommendations for the use of eliglustat in adults with type 1 Gaucher disease in Europe, Eur. J. Int. Med. 37, pp. 25-32, 2017.
Cerdelga Highlights of prescribing information as revised Aug. 2018.
Cerdelga Highlights of prescribing information issued Aug. 2014.
Highlights of Prescribing Information Cerdelga as retrieved from internet on Jun. 2, 2019 from http://www.cerdelga.com/pdf/cerdelga_prescribing_information.pdf.
International Search Report dated Feb. 14, 2019 in PCT/US2018/065423 as filed Dec. 13, 2018.
Li et al., Impact of hepatic and renal impairment on the pharmacokinetics and tolerability of eliglustat therapy for Gaucher disease type 1, Molecular Genetics and Metabolism 129, pp. 117-124, 2020.

* cited by examiner

*Primary Examiner* — Sahar Javanmard
(74) *Attorney, Agent, or Firm* — Kelly L. Bender (57) ABSTRACT

Methods for treating Gaucher disease in patients with renal or hepatic impairment.

9 Claims, 6 Drawing Sheets

METHODS FOR TREATING GAUCHER DISEASE

FIELD OF THE INVENTION

Provided herein are methods for treating Gaucher disease in patients with renal or hepatic impairment.

BACKGROUND OF THE INVENTION

Glycosphingolipids (GSLs) are a class of naturally-occurring compounds which have a multitude of biological functions, including the ability to promote cell growth, cell differentiation, adhesion between cells or between cells and matrix proteins, binding of microorganisms and viruses to cells, and metastasis of tumor cells. GSLs are derived from glucosylceramide (GlcCer), which is produced from ceramide and UDP-glucose by the enzyme UDP-glucose: N-acylsphingosine glucosyltransferase (GlcCer synthase). The structure of ceramide is shown below:

Ceramide

The accumulation of GSL has been linked to a number of diseases, including Tay-Sachs, Gaucher, and Fabry diseases (see, for example, U.S. Pat. No. 6,051,598). Compounds which inhibit glucosylceramide (GlcCer) synthase can lower GSL concentrations and have been reported to be useful for treating a patient with one of the aforementioned diseases.

Eliglustat is a glucosylceramide synthase inhibitor currently approved in the United States as a first-line oral therapy for adults with Gaucher disease type 1 (GD1), who are CYP2D6 extensive metabolizers (EMs), intermediate metabolizers (IMs), or poor metabolizers (PMs).

Eliglustat (chemical name: N-((1R,2R)-1-(2,3-dihydrobenzo[b][1,4]dioxin-6-yl)-1-hydroxy-3-(pyrrolidin-1-yl)propan-2-yl)octanamide) has the structure of Formula (I):

U.S. Pat. No. 7,196,205, for example, describes the preparation and physical and biological properties of the compound of Formula (I).

Eliglustat is sold in the United States under the brand name Cerdelga® as a hemitartrate salt of formula (Ia):

which is also referred to herein as eliglustat tartrate.

The preparation of eliglustat tartrate is described in, for example, WO2011/066352.

The use of eliglustat or a pharmaceutically acceptable salt thereof for treating patients who are CYP2D6 extensive metabolizers (EMs), intermediate metabolizers (IMs), or poor metabolizers (PMs) is described in WO2011/066352.

Eliglustat had not previously been recommended by the FDA and EMA in GD1 patients with hepatic impairment or moderate to severe renal impairment due to lack of data to make dosage recommendations. It has now been surprisingly found that eliglustat can be safely used to treat GD1 in certain patients with hepatic or renal impairment.

SUMMARY OF THE INVENTION

Accordingly, provided herein is a method of treating Gaucher disease comprising administering to a patient in need thereof an effective amount of eliglustat, or a pharmaceutically acceptable salt thereof, wherein said patient is an extensive CYP2D6 metabolizer with mild hepatic impairment (Child-Pugh class A cirrhosis). In one aspect, the effective amount is a twice daily dose of 84 mg of eliglustat, or a pharmaceutically acceptable salt thereof, measured in base form. In one aspect, the Gaucher disease is Gaucher disease type 1.

In another embodiment, provided herein is a method of treating Gaucher disease comprising administering to a patient in need thereof an adjusted effective amount of eliglustat, or a pharmaceutically acceptable salt thereof, wherein said patient is an extensive CYP2D6 metabolizer with mild hepatic impairment and wherein said patient is concurrently taking a drug that is a weak CYP2D6 inhibitor. In one aspect of this embodiment, the adjusted effective amount is a once daily dose of 84 mg of eliglustat or a pharmaceutically acceptable salt thereof, measured in base form. In one aspect, the Gaucher disease is Gaucher disease type 1.

In another embodiment, provided herein is a method of treating Gaucher disease comprising administering to a patient in need thereof an adjusted effective amount of eliglustat, or a pharmaceutically acceptable salt thereof, wherein said patient is an extensive CYP2D6 metabolizer with mild hepatic impairment and wherein said patient is concurrently taking a drug that is strong, moderate, or weak CYP3A inhibitor. In one aspect of this embodiment, the adjusted effective amount is a once daily dose of 84 mg of eliglustat or a pharmaceutically acceptable salt thereof, measured in base form. In one aspect, the Gaucher disease is Gaucher disease type 1.

In another embodiment, provided herein is a method of treating Gaucher disease comprising administering to a patient in need thereof an effective amount of eliglustat, or a pharmaceutically acceptable salt thereof, wherein said patient is an extensive CYP2D6 metabolizer with mild, moderate, or severe renal impairment. In one aspect of this embodiment, the effective amount is a twice daily dose of 84 mg of eliglustat or a pharmaceutically acceptable salt thereof, measured in base form. In one aspect, the Gaucher disease is Gaucher disease type 1.

DETAILED DESCRIPTION OF THE INVENTION

Figure 1:
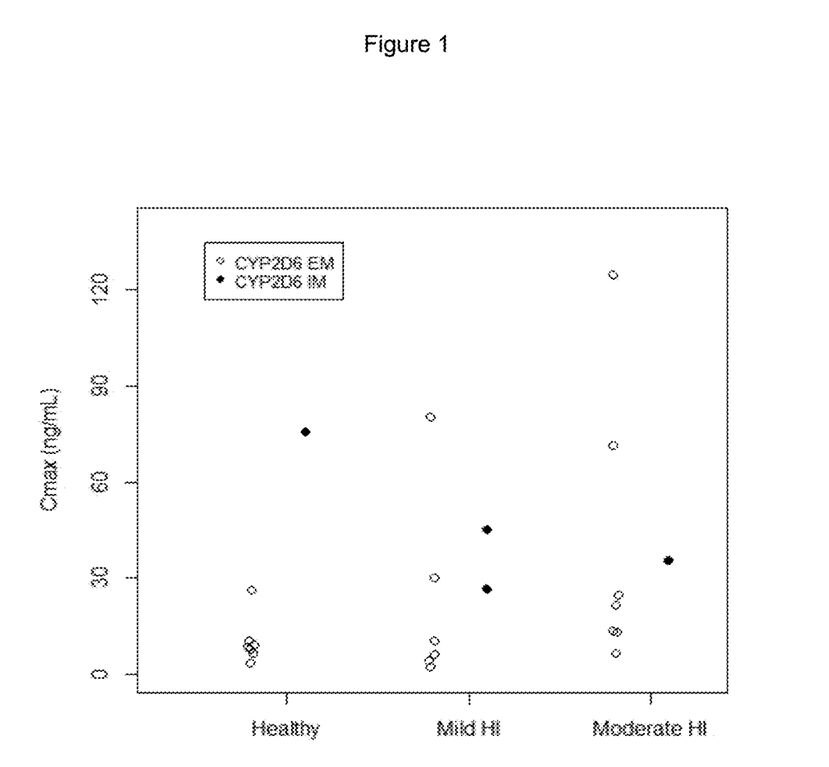
FIG. 1 shows individual $C_{max}$ values after a single dose of 84 mg eliglustat according to the study performed in Example 1.
Figure 2:
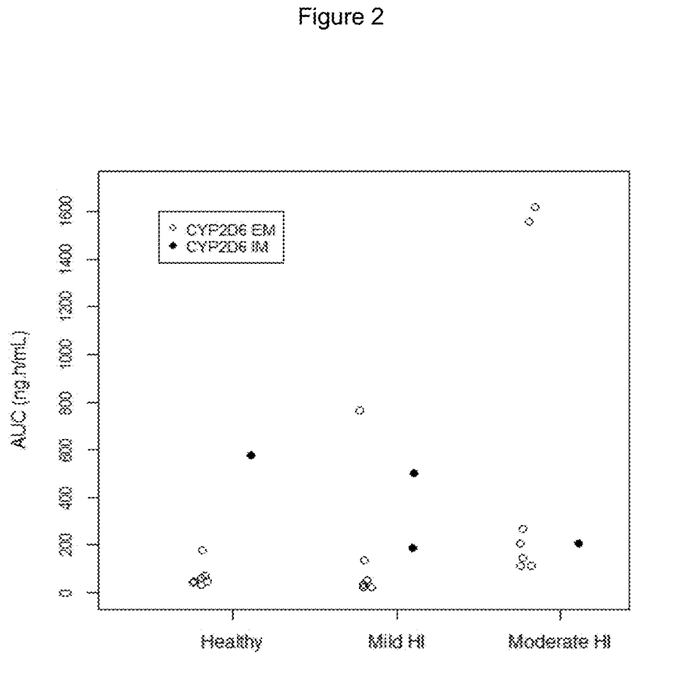
FIG. 2 shows individual AUC values after a single dose of 84 mg eliglustat according to the study performed in Example 1.
Figure 3:
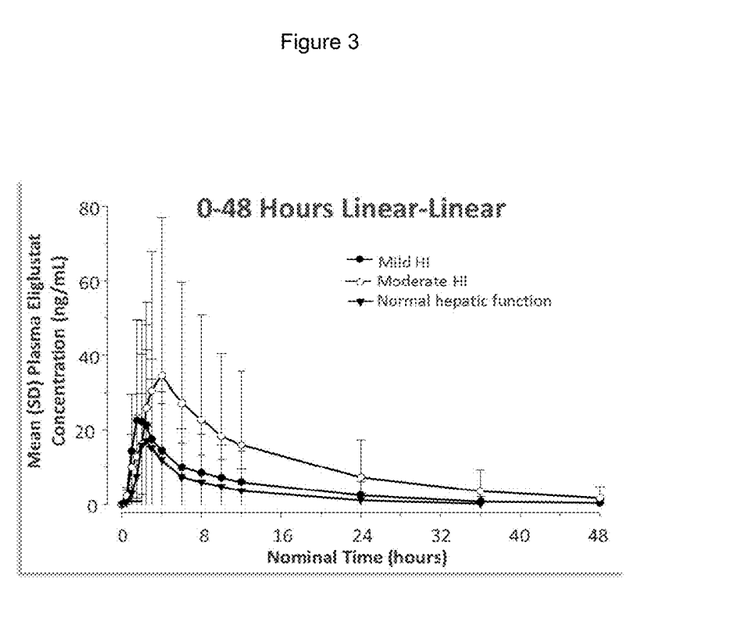
FIG. 3 shows eliglustat concentration-time profiles (mean±SD) by impairment group following a single 84 mg dose of eliglustat according to the study performed in Example 1 (linear-linear scale).
Figure 4:
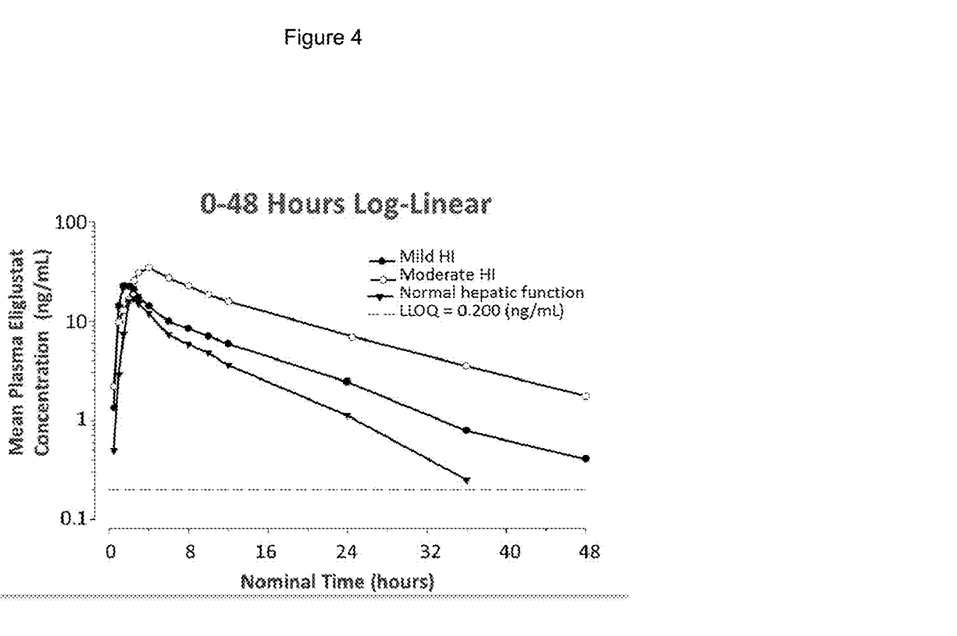
FIG. 4 shows eliglustat concentration-time profiles (mean±SD) by impairment group following a single 84 mg dose of eliglustat according to the study performed in Example 1 (log-linear scale).
Figure 5:
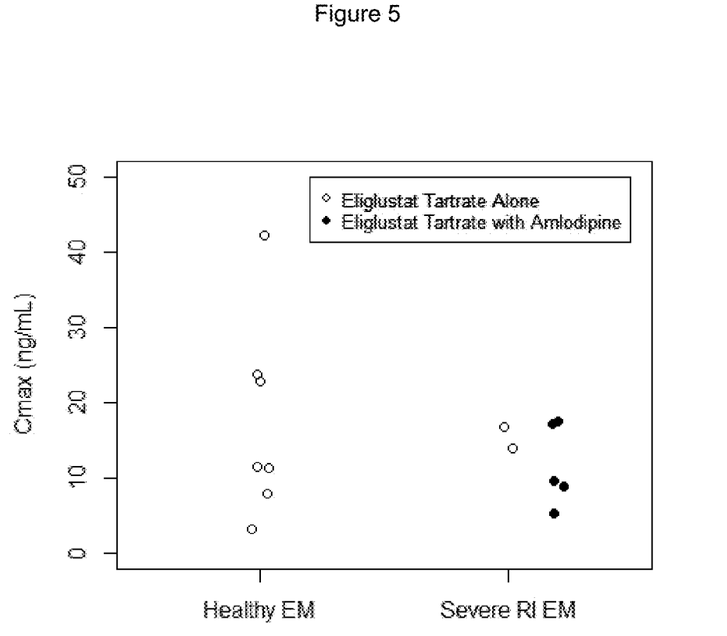
FIG. 5 shows individual $C_{max}$ values after a single dose of 84 mg eliglustat according to the study performed in Example 3.
Figure 6:
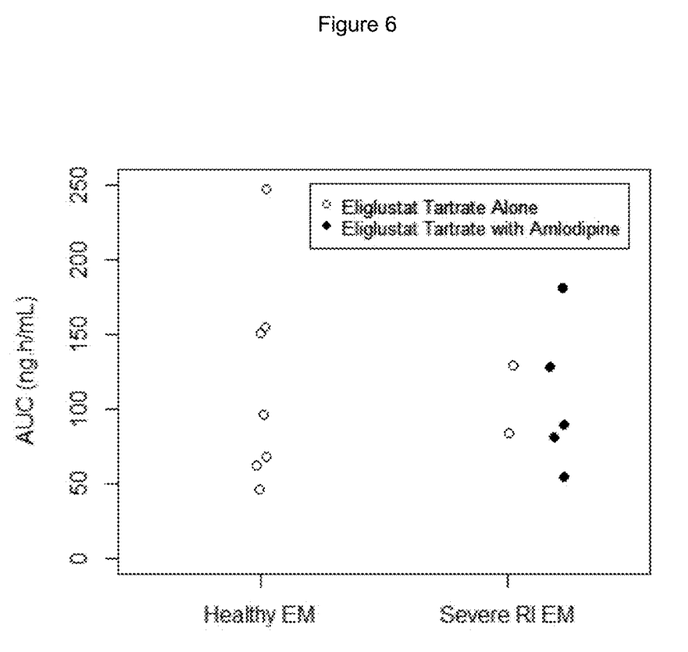
FIG. 6 shows individual AUC values after a single dose of 84 mg eliglustat according to the study performed in Example 3.

As used above, and throughout the description of the invention, the following terms, unless otherwise indicated, shall be understood to have the following meanings:

As used herein, "coadministered," "coadministering," "in combination," and "concurrently taking" means being administered or administering at the same time, in the same day or within a period of 24 hours, particularly within a period of 12 hours.

As used herein, "effective amount" means an amount of eliglustat that would be recommended for a patient to take or a doctor would prescribe the patient to take if the patient does not have hepatic impairment or renal impairment. In one aspect, the effective amount of eliglustat is the amount approved by U.S. Food and Drug Administration, which is 84 mg twice daily to patients who are CYP2D6 EMs or IMs, and which is 84 mg once daily to patients who are PMs. The dose of eliglustat is calculated based on its free base form. It should be understood that eliglustat can be administered as a pharmaceutically acceptable salt, particularly as a hemitartrate, and the amount of salt administered should be adjusted accordingly.

As used herein, "patient" means a human.

"Pharmaceutically acceptable salt" as used herein means that the salts of the compound of the present invention can be used in medicinal preparations.

As used herein, the wording "a compound for use . . . ", for example, shall be understood as being equivalent to the wording "use of a compound for . . . " or "use of a compound for the preparation of a medicament for use in . . . ".

In certain embodiments, a patient's liver function is assessed by the Child-Pugh classification system, which defines three classes of liver cirrhosis. In this classification system, points are assigned to measurements in one of five categories: levels of total bilirubin, serum albumin levels, prothrombin time, ascites, and hepatic encephalopathy. Each measure is given a ranking of 1, 2, or 3, and the sum of the five rankings is the Child-Pugh Score. The Child-Pugh Score is used to classify hepatic impairment by placing patients in a Child-Pugh class: Child-Pugh class A (mild hepatic impairment), Child-Pugh class B (moderate hepatic impairment), and Child-Pugh class C (severe hepatic impairment).

In certain embodiments, a patient's renal function is determined by creatinine clearance calculated by the Cockcroft-Gault formula, wherein a subject or patient with a creatinine clearance of >80 mL/min has normal renal function, and wherein a subject or patient with a creatinine clearance of 50-80 mL/min has mild renal impairment, and wherein a subject or patient with a creatinine clearance of 30-50 mL/min has moderate renal impairment, and wherein a subject or patient with a creatinine clearance of <30 mL/min has severe renal impairment.

Eliglustat is metabolized by the liver, primarily by cytochrome P450 enzymes. Cytochrome P450s ("CYPs") are the principal hepatic xenobiotic metabolizing enzymes. There are eleven xenobiotic-metabolizing cytochrome P450s expressed in a typical human liver (i.e., CYP1A2, CYP2A6, CYP2B6, CYP2C8/9/18/19, CYP2D6, CYP2E1 and CYP3A4/5). Mainly CYP2D6 and to a lesser extent CYP3A4 are the primary cytochrome P450 isoforms that are responsible for metabolizing eliglustat and its pharmaceutically active salts, such as eliglustat tartrate. The level of activity of some P450 enzymes such as CYP2D6 differs according to the individual CYP2D6 phenotype. For example, individuals can be classified as poor, intermediate, extensive, and ultra rapid CYP2D6 metabolizers.

A patient is typically assessed as being a poor, intermediate, extensive, or ultra rapid CYP2D6 metabolizer through genotyping, although rarely the genotype cannot be determined (indeterminate metabolizer).

For example, a patient can be a poor P450 metabolizer as a result of low expression of a P450 enzyme. In such instances, the low expression can be assessed by determining P450 enzyme expression in the patient, i.e., genotyping the patient for the P450 enzyme. For example, expression of CYP2D6 is commonly assessed by PCR (McElroy et. al. "CYP2D6 Genotyping as an Alternative to Phenotyping for Determination of Metabolic Status in a Clinical Trial Setting", AAPS Pharmsi (2000) 2(4) article 33) or by microarray based pharmacogenomic testing. As such, the patient can be conveniently genotyped for P450 expression (e.g., CYP2D6) prior to the initiation of treatment and administered an adjusted effective amount, if necessary.

For the CYP2D6 gene, there are four predicted phenotypes:

As used herein, a "poor CYP2D6 metabolizer" carries two mutant alleles, which result in complete loss of enzyme activity.

As used herein, an "intermediate CYP2D6 metabolizer" possesses one reduced activity allele and one null allele.

As used herein, an "extensive CYP2D6 metabolizer" possesses at least one and no more than two normal functional alleles.

As used herein, an "ultra rapid CYP2D6 metabolizer" carries multiple copies (3-13) of functional alleles and produce excess enzymatic activity.

Because eliglustat is metabolized mainly by CYP2D6 and to a lesser extent by CYP3A, eliglustat concentration may be increased in patients when co-administered with certain drugs that are CYP2D6 enzyme inhibitors. Examples of weak CYP2D6 inhibitors include, but are not limited to, escitalopram, abiraterone, diphenhydramine, amiodarone, deramciclane, desvenlafaxine, fosdevirine, daclatasvir/asunaprevir/beclabuvir, oral contraceptives, osilodrostat, propafenone, ritonavir, cimetidine, clobazam, cobicistat, lorcaserin, celecoxib, felodipine, fluvoxamine, gefitinib, hydroxychloroquine, sertraline, vemurafenib, echinacea, escitalopram, hydralazine, panobinostat, ranitidine, verapamil, alogliptin, diltiazem, dulaglutide, lopinavir/ritonavir, sarpogrelate, artesunate/pyronaridine, imatinib, and febuxostat. Examples of moderate CYP2D6 inhibitors include, but are not limited to, duloxetine, terbinafine, moclobemide, mirabegron, cinacalcet, dronedarone, rolapitant, cimetidine, and tipranavir/ritonavir. Examples of strong CYP2D6 inhibitors include, but are not limited to, paroxetine, fluoxetine, quinidine, bupropion, and dacomitinib.

Patients who are poor CYP2D6 metabolizers have little or no CYP2D6 function, so eliglustat metabolism would primarily be via the CYP3A pathway in these patients.

Eliglustat metabolism in these patients may be further impaired as a result of being treated with certain drugs that are CYP3A enzyme inhibitors. For example, examples of weak CYP3A inhibitors include, but are not limited to, amlodipine, cilostazol, fluvoxamine, goldenseal, isoniazid, ranitidine, and ranolazine. Examples of moderate CYP3A inhibitors include, but are not limited to, erythromycin, ciprofloxacin, fluconazole, diltiazem, verapamil, aprepitant, atazanavir, darunavir, fosamprenavir, imatinib, cimetidine, amprenavir, casopitant, crizotinib, faldaprevir, ledipasvir, netupitant, nilotinib, tofisopam, dronedarone, cimetidine, and cyclosporine. Examples of strong CYP3A inhibitors include, but are not limited to, ketoconazole, clarithromycin, itraconazole, cobicistat, indinavir, lopinavir, ritonavir, saquinavir, telaprevir, tipranavir, posaconazole, voriconazole, telithromycin, conivaptan, boceprevir, idelalisib, mibefradil, nefazodone, nelfinavir, elvitegravir/ritonavir, danopravir/ritonavir, and troleandomycin.

Another embodiment provided herein is a method of providing eliglustat, or a pharmaceutically acceptable salt thereof, wherein the eliglustat, or pharmaceutically acceptable salt thereof, is provided along with information indicating that it is useful for treating patients with Gaucher disease, particularly adult patients with Gaucher disease type 1, and in cases wherein said patient is an extensive CYP2D6 metabolizer with mild hepatic impairment, no dose adjustment is required. In one aspect of this embodiment, the recommended or effective amount is 84 mg of eliglustat, measured as a base, twice daily.

Another embodiment provided herein is a method of providing eliglustat, or a pharmaceutically acceptable salt thereof, wherein the eliglustat, or pharmaceutically acceptable salt thereof, is provided along with information indicating that it is useful for treating patients with Gaucher disease, particularly adult patients with Gaucher disease type 1, and in cases wherein said patient is an extensive CYP2D6 metabolizer with mild hepatic impairment and wherein a weak CYP2D6 inhibitor or a strong, moderate or weak CYP3A inhibitor is coadministered, the effective amount should be reduced to an adjusted effective amount. In one aspect of this embodiment, the adjusted effective amount is 84 mg of eliglustat, measured as a base, once daily.

Another embodiment provided herein is a method of providing eliglustat, or a pharmaceutically acceptable salt thereof, wherein the eliglustat, or pharmaceutically acceptable salt thereof, is provided along with information indicating that eliglustat, or pharmaceutically acceptable salt thereof, is contraindicated in CYP2D6 IMs or PMs with any degree of hepatic impairment and in CYP2D6 EMs with moderate or severe hepatic impairment.

Another embodiment provided herein is a method of providing eliglustat, or a pharmaceutically acceptable salt thereof, wherein the eliglustat, or pharmaceutically acceptable salt thereof, is provided along with information indicating that it is useful for treating patients with Gaucher disease, particularly adult patients with Gaucher disease type 1, and in cases wherein said patient is an extensive CYP2D6 metabolizer with mild, moderate, or severe renal impairment, no dose adjustment is required. In one aspect of this embodiment, the recommended or effective amount is 84 mg of eliglustat, measured as a base, twice daily.

Another embodiment provided herein is a method of providing eliglustat, or a pharmaceutically acceptable salt thereof, wherein the eliglustat, or pharmaceutically acceptable salt thereof, is provided along with information indicating that eliglustat, or pharmaceutically acceptable salt thereof, is not recommended or should be avoided in CYP2D6 EMs with end-stage renal disease and CYP2D6 IMs or PMs with mild, moderate, or severe renal impairment or end-stage renal disease.

Another embodiment provided herein is an article of manufacture comprising
  a) a packaging material;
  b) eliglustat, or a pharmaceutically acceptable salt thereof; and
  c) a label or package insert contained within the packaging material indicating that eliglustat, or a pharmaceutically acceptable salt thereof, is contraindicated in CYP2D6 intermediate metabolizers (IMs) or poor metabolizers (PMs) with any degree of hepatic impairment and in CYP2D6 extensive metabolizers (EMs) with moderate or severe hepatic impairment.

Another embodiment provided herein is an article of manufacture comprising
  a) a packaging material;
  b) eliglustat, or a pharmaceutically acceptable salt thereof; and
  c) a label or package insert contained within the packaging material indicating that no dose adjustment of eliglustat, or a pharmaceutically acceptable salt thereof, is required in CYP2D6 extensive metabolizers (EMs) with mild hepatic impairment.

Another embodiment provided herein is an article of manufacture comprising
  a) a packaging material;
  b) eliglustat, or a pharmaceutically acceptable salt thereof; and
  c) a label or package insert contained within the packaging material indicating that eliglustat, or a pharmaceutically acceptable salt thereof, is contraindicated in extensive metabolizers (EMs) with mild hepatic impairment taking a strong or moderate CYP2D6 inhibitor; and in CYP2D6 extensive metabolizers (EMs) with mild hepatic impairment taking a weak CYP2D6 inhibitor or a strong, moderate or weak CYP3A inhibitor, a dose of 84 mg eliglustat once daily should be considered.

Another embodiment provided herein is an article of manufacture comprising
a) a packaging material;
b) eliglustat, or a pharmaceutically acceptable salt thereof; and
c) a label or package insert contained within the packaging material indicating that no dose adjustment of eliglustat, or a pharmaceutically acceptable salt thereof, is required in CYP2D6 extensive metabolizers with mild, moderate, or severe renal impairment.

Another embodiment provided herein is an article of manufacture comprising
a) a packaging material;
b) eliglustat, or a pharmaceutically acceptable salt thereof; and
c) a label or package insert contained within the packaging material indicating that eliglustat, or a pharmaceutically acceptable salt thereof, is not recommended or should be avoided in CYP2D6 extensive metabolizers (EMs) with end-stage renal disease.

Another embodiment provided herein is an article of manufacture comprising
a) a packaging material;
b) eliglustat, or a pharmaceutically acceptable salt thereof; and
c) a label or package insert contained within the packaging material indicating that eliglustat, or a pharmaceutically acceptable salt thereof, is should be avoided in intermediate metabolizers (IMs) or poor metabolizers (PMs) with mild, moderate or severe renal impairment or end-stage renal disease.

Another embodiment provided herein is a package comprising eliglustat, or a pharmaceutically acceptable salt thereof, and a label, said label comprising a printed statement which informs a prospective user that eliglustat, or pharmaceutically acceptable salt thereof, is i) indicated for the treatment of Gaucher disease type 1 and ii) is contraindicated in CYP2D6 intermediate metabolizers (IMs) or poor metabolizers (PMs) with any degree of hepatic impairment and in CYP2D6 extensive metabolizers (EMs) with moderate or severe hepatic impairment.

Another embodiment provided herein is a package comprising eliglustat, or a pharmaceutically acceptable salt thereof, and a label, said label comprising a printed statement which informs a prospective user that eliglustat, or pharmaceutically acceptable salt thereof, is i) indicated for the treatment of Gaucher disease type 1 and ii) contraindicated in extensive metabolizers (EMs) with mild hepatic impairment taking a strong or moderate CYP2D6 inhibitor. In CYP2D6 extensive metabolizers (EMs) with mild hepatic impairment taking a weak CYP2D6 inhibitor or a strong, moderate or weak CYP3A inhibitor, a dose of 84 mg eliglustat once daily should be considered.

Another embodiment provided herein is a package comprising eliglustat, or a pharmaceutically acceptable salt thereof, and a label, said label comprising a printed statement which informs a prospective user that eliglustat, or pharmaceutically acceptable salt thereof, is i) indicated for the treatment of Gaucher disease type 1 and ii) not recommended or should be avoided in CYP2D6 extensive metabolizers (EMs) with end-stage renal disease (ESRD).

Another embodiment provided herein is a package comprising eliglustat, or a pharmaceutically acceptable salt thereof, and a label, said label comprising a printed statement which informs a prospective user that eliglustat, or pharmaceutically acceptable salt thereof, is i) indicated for the treatment of Gaucher disease type 1 and ii) not recommended in intermediate metabolizers (IMs) or poor metabolizers (PMs) with mild, moderate or severe renal impairment or end-stage renal disease, and eliglustat is not recommended or should be avoided in CYP2D6 extensive metabolizers (EMs) with end-stage renal disease.

Another embodiment provided herein is a method for treating Gaucher disease, comprising administering an adjusted effective amount of eliglustat, or a pharmaceutically acceptable salt thereof, to a patient in need thereof in combination with a weak CYP2D6 inhibitor, wherein said patient is a CYP2D6 extensive metabolizer and wherein said patient has mild hepatic impairment. In one aspect of this embodiment, the adjusted effect amount of eliglustat, or pharmaceutically acceptable salt thereof, is a dose of 84 mg of eliglustat, measured in base form, once daily. In another aspect, the weak CYP2D6 inhibitor is escitalopram, abiraterone, diphenhydramine, amiodarone, deramciclane, desvenlafaxine, fosdevirine, daclatasvir/asunaprevir/beclabuvir, oral contraceptives, osilodrostat, propafenone, ritonavir, cimetidine, clobazam, cobicistat, lorcaserin, celecoxib, felodipine, fluvoxamine, gefitinib, hydroxychloroquine, sertraline, vemurafenib, echinacea, escitalopram, hydralazine, panobinostat, ranitidine, verapamil, alogliptin, diltiazem, dulaglutide, lopinavir/ritonavir, sarpogrelate, artesunate/pyronaridine, imatinib, or febuxostat. In another aspect, the Gaucher disease is Gaucher disease type 1.

Another embodiment provided herein is a method for treating Gaucher disease, comprising administering an adjusted effective dose of eliglustat, or a pharmaceutically acceptable salt thereof, to a patient in need thereof in combination with a strong, moderate or weak CYP3A inhibitor, wherein said patient is a CYP2D6 extensive metabolizer and wherein said patient has mild hepatic impairment. In one aspect of this embodiment, the adjusted effect amount of eliglustat, or pharmaceutically acceptable salt thereof, is a dose of 84 mg of eliglustat, measured in base form, once daily. Examples of weak CYP3A inhibitors include amlodipine, cilostazol, fluvoxamine, goldenseal, isoniazid, ranitidine, and ranolazine. In one aspect, the moderate CYP3A inhibitor is selected from the group consisting of erythromycin, ciprofloxacin, fluconazole, diltiazem, verapamil, aprepitant, atazanavir, darunavir, fosamprenavir, imatinib, cimetidine, amprenavir, casopitant, crizotinib, faldaprevir, ledipasvir, netupitant, nilotinib, tofisopam, dronedarone, cimetidine, and cyclosporine. In one aspect the strong CYP3A inhibitor is selected from the group consisting of ketoconazole, clarithromycin, itraconazole, cobicistat, indinavir, lopinavir, ritonavir, saquinavir, telaprevir, tipranavir, posaconazole, voriconazole, telithromycin, conivaptan, boceprevir, idelalisib, mibefradil, nefazodone, nelfinavir, elvitegravir/ritonavir, danopravir/ritonavir, and troleandomycin. In another aspect, the Gaucher disease is Gaucher disease type 1.

In another embodiment, provided herein is eliglustat or a pharmaceutically acceptable salt thereof for use in treating Gaucher disease in a patient, wherein the patient is an extensive CYP2D6 metabolizer with mild hepatic impairment. In one aspect, eliglustat, or a pharmaceutically acceptable salt thereof, is administered in an effective amount wherein the effective amount is a twice daily dose of 84 mg, measured in base form. In another aspect, the Gaucher disease is Gaucher disease type 1.

In another embodiment, provided herein is eliglustat, or a pharmaceutically acceptable salt thereof, for use in treating Gaucher disease in patient, wherein the patient is an extensive CYP2D6 metabolizer with mild hepatic impairment and wherein said patient is concurrently taking a drug that is a weak CYP2D6 inhibitor. In one aspect, the eliglustat, or a pharmaceutically acceptable salt thereof, is administered in an adjusted effective amount, wherein the adjusted effective amount is a once daily dose of 84 mg of eliglustat, or a pharmaceutically acceptable salt thereof, measured in base form. In another aspect, the weak CYP2D6 inhibitor is selected from escitalopram, abiraterone, diphenhydramine, amiodarone, deramciclane, desvenlafaxine, fosdevirin, daclatasvir/asunaprevir/beclabuvir, oral contraceptives, osilodrostat, propafenone, ritonavir, cimetidine, clobazam, cobicistat, lorcaserin, celecoxib, felodipine, fluvoxamine, gefitinib, hydroxychloroquine, sertraline, vemurafenib, echinacea, escitalopram, hydralazine, panobinostat, ranitidine, verapamil, alogliptin, diltiazem, dulaglutide, lopinavir/ritonavir, sarpogrelate, artesunate/pyronaridine, imatinib, and febuxostat. In another aspect, the Gaucher disease is Gaucher disease type 1.

In another embodiment, provided herein is eliglustat, or a pharmaceutically acceptable salt thereof, for use in treating Gaucher disease in a patient, wherein the patient is an extensive CYP2D6 metabolizer with mild hepatic impairment and wherein said patient is concurrently taking a drug that is strong, moderate, or weak CYP3A inhibitor. In one aspect of this embodiment, the eliglustat, or a pharmaceutically acceptable salt thereof, is administered in an adjusted effective amount, wherein the adjusted effective amount is a once daily dose of 84 mg of eliglustat or a pharmaceutically acceptable salt thereof, measured in base form. In one aspect, the weak CYP3A inhibitor is, for example, selected from amlodipine, cilostazol, fluvoxamine, goldenseal, isoniazid, ranitidine, and ranolazine. In one aspect, the moderate CYP3A inhibitor is, for example, selected from the group consisting of erythromycin, ciprofloxacin, fluconazole, diltiazem, verapamil, aprepitant, atazanavir, darunavir, fosamprenavir, imatinib, and cimetidine. In one aspect the strong CYP3A inhibitor is, for example, selected from the group consisting of ketoconazole, clarithromycin, itraconazole, cobicistat, indinavir, lopinavir, ritonavir, saquinavir, telaprevir, tipranavir, posaconazole, voriconazole, telithromycin, conivaptan, and boceprevir. In another aspect, the Gaucher disease is Gaucher disease type 1.

In another embodiment, provided herein is eliglustat or a pharmaceutically acceptable salt thereof for use in treating Gaucher disease in a patient, wherein the patient is an extensive CYP2D6 metabolizer with mild, moderate, or severe renal impairment. In one aspect of this embodiment, the eliglustat, or a pharmaceutically acceptable salt thereof, is administered in an effective amount, wherein the effective amount is a twice daily dose of 84 mg of eliglustat or a pharmaceutically acceptable salt thereof, measured in base form. In another aspect, the Gaucher disease is Gaucher disease type 1.

For their therapeutic use, eliglustat and pharmaceutically acceptable salts thereof are generally introduced into pharmaceutical compositions.

These pharmaceutical compositions comprise eliglustat or a pharmaceutically acceptable salt thereof and one or more pharmaceutically acceptable excipients.

Said excipients are chosen according to the pharmaceutical form and the method of administration desired, from the usual excipients which are known to those skilled in the art.

By way of example, a dose of eliglustat or a pharmaceutically acceptable salt thereof, in capsule form, may correspond to the following example: A capsule for oral use comprising 84 mg of eliglustat (equivalent to 100 mg of the hemitartrate salt), microcrystalline cellulose, lactose monohydrate, hypromellose and glyceryl behenate.

The present invention may be better understood by reference to the following non-limiting examples, which is exemplary of the invention. It should in no way be construed, however, as limiting the breath of the scope of the invention.

Example 1

A multi-center, open-label, single oral dose study of eliglustat tartrate administered to mild or moderate HI and normal hepatic function (healthy) matched (by body weight and cytochrome P450 [CYP] 2D6 phenotype) subjects was carried out to study the effect of mild and moderate hepatic impairment (HI) on the pharmacokinetics (PK) of eliglustat.

Approximately 8 subjects were planned to be enrolled into each HI group (mild or moderate HI) and 8 subjects with normal hepatic function matched to impaired subjects by weight and CYP2D6 phenotype. At least 6 CYP2D6 extensive metabolizers (EMs) were to be enrolled into each impairment group, with the remaining 2 subjects enrolled according to the following preference: at least 20 subjects were to be screened for each impairment group and if identified, up to 2 CYP2D6 poor metabolizers (PMs) were enrolled. If less than 2 PMs were identified, up to 2 CYP2D6 intermediate metabolizers (IMs) were to be enrolled for a total of 8 subjects per group. If less than 2 PMs or IMs were identified, up to 2 additional EMs were to be enrolled for a total of 8 subjects per group. If 2 PMs were identified prior to screening 20 subjects, screening may have been discontinued. If an eligible PM subject was identified after satisfying the above requirements and enrolling 8 subjects for an impairment group, this subject may still have been enrolled for that impairment group.

CYP2D6 EMs and IMs were to receive a single 100-mg dose of eliglustat tartrate, while CYP2D6 PMs were to receive a single 50-mg dose of eliglustat tartrate.

Diagnosis and Criteria for Inclusion:

For HI subjects: Male (body weight between 50.0 and 125.0 kg, inclusive) or female subjects (body weight between 40.0 and 110.0 kg, inclusive) between 18 and 79 years, inclusive, with a body mass index between 18.0 and 37 kg/m$^2$, inclusive; having stable chronic liver disease assessed by medical history, physical examination, and laboratory values; with moderate HI (defined as Child-Pugh score of 7 to 9, inclusive) or mild HI (defined as Child-Pugh score of 5 to 6, inclusive). For healthy subjects: Male or female subjects, between 18 and 79 years, inclusive; body weight within 15% of the body weight of matched subjects with HI, and body mass index between 18.0 and 37 kg/m$^2$, inclusive; healthy subjects were also matched to HI groups by CYP2D6 phenotype predicted from genotype.

Dose Regimen:

A single 100-mg capsule of eliglustat tartrate (equivalent to 84 mg of eliglustat) was administered to CYP2D6 EM or IM subjects with mild or moderate HI and matching healthy subjects.

A single 50-mg capsule of eliglustat tartrate (equivalent to 42 mg of eliglustat) was to be administered to CYP2D6 PM with mild or moderate HI and matching healthy subjects.

Criteria for Evaluation:

Pharmacokinetics: The following PK parameters were calculated for eliglustat plasma concentrations using non-compartmental methods: Maximum plasma concentration observed ($C_{max}$), area under the plasma concentration versus time curve calculated using the trapezoidal method from time zero to the time corresponding to the last quantifiable concentration $t_{last}$ ($AUC_{last}$), time to reach $C_{max}$($t_{max}$), area under the plasma concentration versus time curve extrapolated to infinity (AUC), terminal half-life associated with the terminal slope $\lambda z$ ($t_{1/2z}$), time corresponding to the last concentration above the limit of quantification ($t_{last}$), apparent total body clearance of a drug from the plasma (CL/F), and apparent volume of distribution during the terminal ($\lambda z$) phase (Vz/F).

Pharmacokinetic Sampling Times and Bioanalytical Methods:

Blood samples were collected at the following timepoints to assess plasma concentrations of eliglustat: predose and 0.5, 1, 1.5, 2, 2.5, 3, 4, 6, 8, 10, 12, 24, 36, and 48 hours postdose.

Eliglustat concentrations in plasma were determined using a validated liquid chromatography-tandem mass spectrometry method with a lower limit of quantification of 0.2 ng/mL.

Statistical Methods:

Pharmacokinetics

Eliglustat PK parameters were summarized using descriptive statistics for each population group and for each CYP2D6 phenotype. For log-transformed $C_{max}$, $AUC_{last}$, AUC, $t_{1/2z}$, CL/F and Vz/F, the effect of hepatic impairment on a single dose of eliglustat tartrate on eliglustat PK parameters were analyzed using a linear fixed effects model for CYP2D6 EM subjects. Estimate and 90% confidence interval (CI) for geometric mean of each population group and also for the geometric mean ratio of each hepatic impaired group versus the normal control group were provided for each parameter.

Safety

The safety evaluation was based upon the review of the individual values (clinically significant abnormalities) and descriptive statistics (summary tables). All safety analyses were performed using the safety population and were based on the on-treatment phase (defined as the time from investigational medicinal product [IMP] administration up to Day 3 visit, inclusive). For laboratory, vital signs, and ECG data, potentially clinically significant abnormalities (PCSAs) were analyzed using the 24 May 2014 version of the PCSA list. Electrocardiogram parameters were obtained from automatic reading of 12-lead ECGs and were analyzed as raw parameter values and change from baseline. For vital signs, raw data and changes from baseline were summarized using descriptive statistics by population group and time point. All individual data for biochemistry, hematology, and qualitative urinary tests were listed.

Adverse events were coded according to the Medical Dictionary for Regulatory Activities (MedDRA v.19.1) and classified into predefined standard categories according to chronological criteria:

Pretreatment adverse events (AEs), defined as AEs that occurred, worsened (according to Investigator opinion), or became serious during the pretreatment phase (defined as the time between the signature of the informed consent and IMP administration [excluded]);

Treatment-emergent AEs (TEAEs), defined as AEs that occurred, worsened, or became serious during the on-treatment phase;

Posttreatment AEs, defined as AEs that occurred, worsened, or became serious during the posttreatment phase (defined as the time after Day 3 visit through completion of EOS).

All AEs reported in the study were listed and sorted by subject, onset date and time. The number and percentage of subjects with TEAEs were listed by population group, primary system-organ class (SOC), preferred term (PT), and AE diagnosis.

Population Characteristics:

Eight subjects were enrolled into each group. Seven CYP2D6 EMs and 1 CYP2D6 IM, each, were enrolled into the moderate impairment group and the healthy matched group, and 6 CYP2D6 EMs and 2 CYP2D6 IMs were enrolled into the mild impairment group.

Pharmacokinetic Results:

Mean±SD (Geometric Mean) [CV %] PK parameters of eliglustat in CYP2D6 EM subjects after a single dose of 100 mg eliglustat tartrate

| | Plasma Eliglustat | | | | | |
|---|---|---|---|---|---|---|
| | CYP2D6 EM Subjects | | | CYP2D6 IM Subjects | | |
| Parameter | Healthy | Mild HI | Moderate HI | Healthy | Mild HI | Moderate HI |
| N | 7 | 6 | 7 | 1 | 2 | 1 |
| $C_{max}$ (ng/mL) | 10.4 ± 7.40 (8.81) [70.9] | 22.4 ± 30.2 (10.7) [135.1] | 39.5 ± 43.4 (24.8) [110.0] | 75.9 | 35.9 (26.7, 45.1) | 35.6 |
| $t_{max}^a$ (h) | 2.50 (1.00-3.00) | 1.75 (1.00-6.00) | 4.00 (1.00-6.00) | 2.50 | 2.00 (2.00, 2.00) | 1.52 |
| $AUC_{last}$ (ng · h/mL) | 63.9 ± 47.1 (54.7) [73.7] | 166 ± 285 (64.3) [171.3] | 536 ± 642 (293) [119.6] | 568 | 334 (187, 481) | 197 |
| AUC (ng · h/mL) | 69.0 ± 49.1 (59.5) [71.2] | 172 ± 293 (68.5) [170.5] | 575 ± 696 (307) [121.0] | 578 | 346 (190, 501) | 208 |
| $t_{1/2z}$ (h) | 7.08 ± 0.881 (7.03) [12.5] | 7.25 ± 1.46 (7.13) [20.1] | 10.5 ± 2.25 (10.3) [21.4] | 8.48 | 9.34 (8.27, 10.4) | 5.87 |
| CL/F (L/h) | 1570 ± 628 (1420) [40.1] | 1980 ± 1440 (1230) [72.8] | 416 ± 295 (275) [70.9] | 146 | 306 (168, 444) | 406 |
| Vz/F (L) | 16030 ± 6020 (14400) [37.5] | 20000 ± 15600 (12700) [78.2] | 5840 ± 4130 (4090) [70.7] | 1790 | 3910 (2520, 5300) | 3430 |
| $t_{last}^a$ (h) | 24.00 (24.00-24.05) | 30.00 (24.00-48.00) | 48.00 (36.00-48.00) | 48.00 | 48.00 (48.00, 48.00) | 24.00 |

$^a$Median (Min – Max)

b Mean (Min, Max) for N = 2

| Point estimates of geometric mean ratio with 90% CI in CYP2D6 EM subjects | | | |
|---|---|---|---|
| Parameter | Comparison | Estimate | 90% CI |
| $C_{max}$ | Mild HI vs Healthy | 1.22 | (0.46 to 3.23) |
| | Moderate HI vs Healthy | 2.81 | (1.10 to 7.17) |
| $AUC_{last}$ | Mild HI vs Healthy | 1.18 | (0.42 to 3.28) |
| | Moderate HI vs Healthy | 5.35 | (2.00 to 14.35) |
| AUC | Mild HI vs Healthy | 1.15 | (0.41 to 3.19) |
| | Moderate HI vs Healthy | 5.16 | (1.93 to 13.74) |
| $t_{1/2z}$ | Mild HI vs Healthy | 1.01 | (0.85 to 1.21) |
| | Moderate HI vs Healthy | 1.47 | (1.24 to 1.74) |
| CL/F | Mild HI vs Healthy | 0.87 | (0.31 to 2.41) |
| | Moderate HI vs Healthy | 0.19 | (0.07 to 0.52) |

-continued

| Point estimates of geometric mean ratio with 90% CI in CYP2D6 EM subjects | | | |
|---|---|---|---|
| Parameter | Comparison | Estimate | 90% CI |
| Vz/F | Mild HI vs Healthy | 0.88 | (0.34 to 2.29) |
| | Moderate HI vs Healthy | 0.28 | (0.11 to 0.71) |

Compared to healthy CYP2D6 EMs, eliglustat mean $C_{max}$ and AUC was slightly higher in CYP2D6 EMs with mild HI (1.22 and 1.15 fold, respectively) and appreciably higher in subjects with moderate HI (2.81 and 5.16 fold, respectively) following a single 100-mg dose of eliglustat tartrate. Mean $t_{1/2z}$ values were similar in mild HI subjects and healthy subjects, but were prolonged in moderate HI subjects (10.5 hours versus 7.08 hours).

Safety Results:

A total of 6 mild TEAEs were observed in 5 subjects. Four TEAEs in 3 subjects were considered related to study drug by the investigator: dysgeusia in 2 subjects with moderate HI and nausea and headache in 1 healthy subject. No serious adverse events were reported, and there were no deaths or other significant AEs. There were no treatment emergent PCSA that were clinically relevant for the laboratory values or for vital signs and ECGs.

Example 2

A physiologically-based pharmacokinetic (PBPK) model developed using eliglustat preclinical and clinical study results was verified using the observed single-dose data in both healthy and hepatic impaired patients from the study described in Example 1. This PBPK model was used to predict eliglustat exposures after repeated dosing of eliglustat in CYP2D6 EM subjects with mild and moderate HI as well as in CYP2D6 EM healthy subjects (without HI) for comparison. Simulation of eliglustat PK was conducted with 10 virtual trials of 10 subjects/category after repeated dosing of 84 mg twice daily (BID) or once daily (QD) eliglustat oral dose alone for 8 days, and the simulation results are presented in Table 1.

TABLE 1

Simulated Mean (Range of the 10 Means of the 10 Trials) Steady-State Exposure after Oral Administration of Eliglustat in CYP2D6 EMs (Healthy, Mild HI and Moderate HI)

| | 84 mg BID[a] | | Ratio[b] (HI/Healthy) | | 84 mg QD[a] | |
|---|---|---|---|---|---|---|
| CYP2D6 EM | $C_{max}$ (ng/mL) | $AUC_{0\text{-}tau}$ (ng·h/mL) | $C_{max}$ | $AUC_{0\text{-}tau}$ | $C_{max}$ (ng/mL) | $AUC_{0\text{-}tau}$ (ng·h/mL) |
| Healthy | 27 (17.0, 37.2) | 199 (114, 291) | — | — | 17.9 (12.7, 22.2) | 146 (94.5, 203) |
| Mild HI | 64.2 (39.1, 97.0) | 568 (322, 893) | 2.38 | 2.85 | 32.9 (22.2, 49.5) | 351 (215, 606) |
| Moderate HI | 173 (127, 235) | 1760 (1270, 2470) | 6.41 | 8.86 | 83.5 (59.2, 115) | 1270 (852, 1890) |

$AUC_{0\text{-}tau}$ = area under the plasma concentration versus time curve from time zero to the end of the dosing interval of 12 hours for BID and 24 hours for QD ($AUC_{0\text{-}tau}$ represents $AUC_{0\text{-}12}$ for BID regimen and $AUC_{0\text{-}24}$ for QD regimen);
BID = twice daily;
$C_{max}$ = maximum observed plasma concentration;
EM = extensive metabolizer;
QD = once daily;
HI = hepatic impairment
[a]Values are reported to 3 significant figures
[b]Ratio of the mean exposures To ensure that eliglustat exposure will remain within the range of eliglustat exposures that has been demonstrated to be safe and efficacious in the clinical development program, 84 mg QD of eliglustat when coadministered with CYP2D6 inhibitors or CYP3A inhibitors was evaluated using PBMK modeling for CYP2D6 EM subjects with mild HI. Various scenarios of coadministration of eliglustat 84 mg QD with CYP2D6 inhibitors or CYP3A inhibitors were simulated using Simcyp build-in model of inhibitors with minor modifications as needed. Paroxetine, terbinafine, and ritonavir were used as strong, moderate, and weak CYP2D6 inhibitors, respectively, while ketoconazole, fluconazole, and fluvoxamine were used as strong, moderate, and weak CYP3A inhibitors, respectively. Simulation of eliglustat PK was conducted with 10 virtual trials of 10 CYP2D6 EM subjects with mild HI after repeated dosing of 84 mg QD eliglustat alone for 8 days (from Day 1 to Day 8) and with CYP2D6 or CYP3A inhibitors for an additional 7 or 10 days (Day 9 to Day 15 or Day 9 to Day 18). The PBPK-predicted eliglustat mean (range of the means of the 10 virtual trials) exposures in CYP2D6 EMs with mild HI upon coadministration of eliglustat with CYP2D6 or CYP3A inhibitors are presented in Table 2. Simulated exposures in healthy EMs and EMs with mild HI following eliglustat alone at 84 mg BID were also included for comparison.

TABLE 2

Simulated Mean (Range of the 10 Means of the 10 Trials) Steady-State Exposure in CYP2D6 EMs (Heathy and Mild HI) after Oral Administration of Eliglustat with and without CYP2D6 or CYP3A Inhibitors

| Eliglustat | Population | CYP Inhibitor Type | CYP Inhibitor (dose) | Eliglustat + CYP Inhibitor $C_{max}^a$ (ng/mL) | Eliglustat + CYP Inhibitor $AUC_{0\text{-}tau}^a$ (ng · h/mL) |
|---|---|---|---|---|---|
| 84 mg BID | Healthy | None | — | 27 (17.0, 37.2) | 199 (114, 291) |
| 84 mg BID | Mild HI | None | — | 64.2 (39.1, 97.0) | 568 (322, 893) |
| 84 mg QD | Mild HI | Strong CYP2D6 inhibitor | Paroxetine (30 mg QD) | 155 (119, 192) | 2630 (1840, 3450) |
| 84 mg QD | Mild HI | Strong CYP3A inhibitor | Ketoconazole (400 mg QD) | 71.7 (32.8, 138) | 1060 (377, 2380) |
| 84 mg QD | Mild HI | Moderate CYP2D6 inhibitor | Terbinafine (250 mg QD) | 96.9 (82.1, 110) | 1350 (1080, 1580) |
| 84 mg QD | Mild HI | Moderate CYP3A inhibitor | Fluconazole (400 mg loading dose + 200 mg QD) | 53.5 (31.6, 83.7) | 700 (342, 1240) |
| 84 mg QD | Mild HI | Weak CYP2D6 inhibitor | Ritonavir (100 mg BID) | 45.5 (31.0, 64.9) | 529 (361, 797) |
| 84 mg QD | Mild HI | Weak CYP3A inhibitor | Fluvoxamine (300 mg QD) | 42.4 (26.4, 65.9) | 482 (281, 850) |

$AUC_{0\text{-}tau}$ = area under the plasma concentration versus time curve from time zero to the end of the dosing interval of 12 hours for BID and 24 hours for QD ($AUC_{0\text{-}tau}$ represents $AUC_{0\text{-}12}$ for BID regimen and $AUC_{0\text{-}24}$ for QD regimen);
BID = twice daily;
$C_{max}$ = maximum observed plasma concentration;
QD = once daily.
$^a$Values were reported to 3 significant figures Example 3

A phase 1, open-label, 2-stage, pharmacokinetic and tolerability study of single dose eliglustat tartrate in subjects with renal impairment (RI) (mild, moderate, and severe) and subjects with normal renal function, matched to RI subjects by age, weight, and cytochrome P450 [CYP] 2D6 phenotype was carried out to study the effect of mild, moderate, and severe RI on the pharmacokinetics (PK) of eliglustat.

Methodology: A phase 1, open-label, 2-stage, pharmacokinetic and tolerability study of single dose eliglustat tartrate in subjects with renal impairment (RI) (mild, moderate, and severe) and subjects with normal renal function, matched to RI subjects by age, weight, and cytochrome P450 [CYP] 2D6 phenotype.

Approximately 32 subjects were planned to be enrolled in 2 stages: Stage 1 comprised of 8 subjects with severe RI and 8 subjects with normal renal function, matched by CYP2D6 phenotype, weight, and age. Subjects with mild and moderate RI would have been enrolled in Stage 2 if the results in subjects with severe RI showed a substantial effect of reduced renal function on eliglustat PK compared to the matched normal function subjects. Stage 2 was to include 8 subjects with mild and 8 subjects with moderate RI. Each cohort was to enroll at least 6 CYP2D6 extensive metabolizers (EMs). The remaining 2 subjects were to be poor metabolizers (PMs), intermediate metabolizers (IMs) or EMs, enrolled according to the following preference: at least 20 subjects were to be screened for each cohort and if identified, up to 2 PMs were to be enrolled. If less than 2 PMs were identified, up to 2 IMs were to be enrolled for a total of 8 subjects. If less than 2 PMs and IMs were identified, up to 2 additional EMs were to be enrolled for a total of 8 subjects. Allowed concomitant medications included no more than one weak CYP3A inhibitor and one weak CYP2D6 inhibitor, alone or in combination.

CYP2D6 EMs and IMs were to receive a single 100 mg dose of eliglustat tartrate while CYP2D6 PMs were to receive a single 50 mg dose of eliglustat tartrate.

Diagnosis and Criteria for Inclusion:

For RI subjects: Male (body weight between 50.0 and 125.0 kg, inclusive) and female (body weight between 40.0 and 110.0 kg, inclusive) subjects between 18 and 79 years, with a body mass index (BMI) between 18.0 and 37.0 kg/m2, inclusive, having mild, moderate or severe RI determined by a creatinine clearance (CrCl), calculated by Cockcroft-Gault formula, of 50-80 mL/min, 30-50 mL/min or <30 mL/min, respectively.

Normal renal function subjects: Male or female subjects, between 18 and 79 years, inclusive, body weight within 15% of the body weight of matched subject with RI, BMI between 18.0 and 37.0 kg/m$^2$ and a CrCl of >80 mL/min. Healthy subjects were also matched by age and CYP2D6 predicted phenotype based on genotype.

Dose Regimen:

A single 100 mg capsule of eliglustat tartrate (equivalent to 84 mg of eliglustat) was to be administered to CYP2D6 EM or IM subjects with RI and matching healthy subjects.

A single 50 mg capsule of eliglustat tartrate (equivalent to 42 mg of eliglustat) was to be administered to CYP2D6 PM subjects with RI and matching healthy subjects.

Criteria for Evaluation:

Pharmacokinetics: Plasma eliglustat concentrations were used to determine the following PK parameters using non-compartmental methods: Maximum plasma concentration observed ($C_{max}$), first time to reach $C_{max}$ ($t_{max}$), area under the plasma concentration versus time curve calculated using the trapezoidal method from time zero to the time corresponding to the last concentration above the limit of quantification, $t_{last}$ ($AUC_{last}$), area under the plasma concentration time curve extrapolated to infinity (AUC), terminal half-life associated with the terminal slope Xz ($t_{1/2z}$), apparent total body clearance of a drug from plasma (CL/F), and apparent volume of distribution during the terminal phase (VZ/F).

Pharmacokinetic/Pharmacodynamics Sampling Times and Bioanalytical Methods:

Blood samples were collected at the following time points to assess plasma concentrations of eliglustat: predose, and 0.5, 1, 1.5, 2, 2.5, 3, 4, 6, 8, 10, 12, 24, and 36 hours postdose.

Eliglustat concentrations in plasma were determined using a validated liquid chromatography tandem mass spectrometry method with a lower limit of quantification (LLOQ) of 0.2 ng/mL.

Statistical Methods:
Pharmacokinetics:

Eliglustat PK parameters were summarized using descriptive statistics for each population group and for each CYP2D6 phenotype. For log-transformed $C_{max}$, $AUC_{last}$, AUC, $t_{1/2z}$, CL/F, and Vz/F, the effect of severe RI on eliglustat PK parameters after a single dose of eliglustat tartrate was analyzed using a linear fixed effects model on CYP2D6 EM subjects. Inclusion of population, CYP3A weak inhibitor, age, and weight as covariate was selected manually, choosing the model with the lowest AIC value. After testing, the final model chosen were those with only population as fixed term. Estimate and 90% confidence interval (CI) for the geometric mean of each population group and for the geometric mean ratio of severe RI group versus the normal control group were provided from this model for each parameter.

Safety:

The safety evaluation was based on the review of the individual values (clinically significant abnormalities) and descriptive statistics (summary tables). All safety analyses were performed using the safety population and based on the on-treatment phase (defined as the start time of investigational medicinal product [IMP] administration up to Day 3 visit). For laboratory, vital sign, and ECG data, the Potentially Clinically Significant Abnormalities (PCSAs) were analyzed using PCSA list (Version 3.0, 24 May 2014). Electrocardiogram parameters were obtained from automatic reading of the 12-lead ECGs and were analyzed as raw parameter value and change from baseline. For vital signs, raw data and changes from baseline were summarized using descriptive statistics by population group and time of measurement. All individual data for biochemistry, hematology, and qualitative urinary tests were listed.

Vital signs and ECG readings were analyzed as raw parameter value and change from baseline.

Adverse events were coded according to the Medical Dictionary for Regulatory Activities (MedDRA, version 19.1). They were classified into pre-defined standard categories according to chronological criteria:

Pretreatment adverse events: AEs that occurred, worsened (according to the Investigator's opinion) or became serious during the pretreatment phase (defined as the time between the signature of the informed consent and IMP administration [excluded]);

Treatment-emergent adverse events (TEAEs): AEs that occurred, worsened or became serious during the on-treatment phase;

Posttreatment adverse events: AEs that occurred, worsened or became serious during the posttreatment phase (defined as starting after the Day 3 visit and ending with EOS).

The number and percentage of subjects with TEAEs were listed by population group, primary system-organ class (SOC), preferred term (PT), and AE diagnosis.

Population Characteristics:

A total of 16 subjects were enrolled: 8 subjects were enrolled into the severe RI cohort and 8 into the healthy matched cohort. For each cohort, 7 subjects were CYP2D6 EMs and 1 subject was CYP2D6 IM. Since Stage 1 did not show a substantial effect of severe RI on eliglustat PK compared to the matched normal renal function in EMs, Stage 2 of the study was not undertaken. Five EMs subjects in the severe RI cohort were concomitantly taking a weak CYP3A inhibitor (amlodipine) and 1 IM subject in the severe renal impairment cohort was taking both a weak CYP2D6 inhibitor (escitalopram) and a weak CYP3A inhibitor (amlodipine). None of the healthy matched subjects were taking CYP2D6 or CYP3A inhibitors.

Pharmacokinetic results:
Mean ± SD (Geometric Mean) [CV %] plasma
PK parameters of eliglustat after a single
oral dose of 100 mg eliglustat tartrate

| Parameter | CYP2D6 EM Subjects | | CYP2D6 IM Subjects | |
|---|---|---|---|---|
| | Healthy | Severe RI | Healthy | Severe RI |
| N | 7 | 7 | 1 | 1 |
| $C_{max}$ (ng/mL) | 17.6 ± 13.2 (13.4) [75.2] | 12.7 ± 4.85 (11.8) [38.1] | 54.7 | 220 |
| $t_{max}{}^a$ (h) | 1.50 (0.50-6.00) | 4.00 (1.00-6.00) | 3 | 4 |
| $AUC_{last}$ (ng·h/mL) | 112 ± 68.7 (96.0) [61.1] | 102 ± 41.7 (95.5) [40.7] | 520 | 3590 |
| AUC (ng·h/mL) | 118 ± 71.1 (101) [60.3] | 107 ± 42.1 (99.8) [39.5] | 559 | $NR^b$ |
| $t_{1/2z}$ (h) | 8.50 ± 1.51 (8.39) [17.8] | 6.56 ± 0.876 (6.51) [13.3] | 9.59 | $NR^b$ |
| CL/F (L/h) | 963 ± 532 (834) [55.2] | 903 ± 354 (845) [39.2] | 151 | $NR^b$ |
| Vz/F (L) | 11700 ± 6710 (10100) [57.5] | 8480 ± 3190 (7940) [37.7] | 2090 | $NR^b$ |
| $t_{last}{}^a$ (h) | 36.00 (24.00-36.00) | 36.00 (24.00-36.00) | 36.00 | 36.00 |

$^a$Median (Min-Max)
$^b$NR: not reported. AUC, CL/F, $t_{1/2}$ and $V_z$/F values were not reported due to % AUC extrapolation greater than 20% of total AUC Point estimates of geometric mean ratio
with 90% CI in CYP2D6 EM subjects

| Comparison | Parameter | Estimate | 90% CI |
|---|---|---|---|
| Severe RI vs Healthy | $C_{max}$ | 0.878 | (0.462 to 1.669) |
| | $AUC_{last}$ | 0.994 | (0.608 to 1.627) |
| | AUC | 0.986 | (0.609 to 1.597) |
| | $t_{1/2z}$ | 0.776 | (0.671 to 0.898) |
| | CL/F | 1.014 | (0.626 to 1.643) |
| | Vz/F | 0.787 | (0.485 to 1.275) |

Note:
The analysis model is log(PK parameter) = Population and conducted for EM subjects (7 severe RI and 7 Healthy).

Eliglustat geometric mean $C_{max}$ and AUC values were similar in subjects with severe RI and healthy matched subjects with CYP2D6 EM phenotype (0.878 and 0.986 fold, respectively). Coadministration of a single weak CYP3A inhibitor (amlodipine) in CYP2D6 EM subjects with severe RI (N=5, geometric mean [CV %] for $C_{max}$ and AUC: 10.6 ng/mL [46.6] and 98.3 ng·h/mL [45.9], respectively) did not appear to result in an increase in eliglustat exposures compared to severe RI EM subjects receiving eliglustat tartrate alone (N=2, geometric mean [CV %] for $C_{max}$ and AUC: 15.2 ng/mL [12.9] and 104 ng·h/mL [30.3], respectively). Mean $t_{1/2z}$ values were shorter in severe RI subjects than in healthy subjects (6.56 versus 8.50 hours) and $t_{max}$ values were longer (4.0 versus 1.5 hours).

No definitive conclusion can be drawn for the effect of RI in CYP2D6 IMs as only one CYP2D6 IM with severe RI taking concomitant medications was included. The substantially higher $AUC_{last}$ values in this subject compared to CYP2D6 IM healthy subject (6.90-fold) or to either healthy CYP2D6 EMs (32.1-fold) or CYP2D6 EM with severe RI (35.2-fold) is attributed, at least in part, to the combined effect of 2 coadministered CYP inhibitors, a CYP2D6 inhibitor (escitalopram) and a CYP3A inhibitor (amlodipine).

Safety Results:

A total of one mild TEAE was observed in 1 subject, and was considered related to study drug by the investigator: fatigue in a healthy subject. No serious adverse events were reported, and there were no deaths or withdrawals due to AEs. There were no treatment emergent PCSA that were clinically relevant for the laboratory values or for vital signs and ECGs.

Overall Conclusion:

The effects of mild and moderate hepatic impairment in a subject were evaluated in a single dose phase 1 study described in Example 1. After a single 84 mg dose, eliglustat $C_{max}$ and AUC were 1.22- and 1.15-fold higher in CYP2D6 EMs with mild hepatic impairment, and 2.81- and 5.16-fold higher in CYP2D6 EMs with moderate hepatic impairment compared to healthy CYP2D6 EMs.

Steady state exposures were predicted in CYP2D6 EMs with mild and moderate hepatic impairment using the PBPK model. Doses of eliglustat that would result in the mean steady state exposures within the efficacious and safe exposure ranges were proposed for CYP2D6 EMs with hepatic impairment when eliglustat is administered alone or with CYP inhibitors. Therefore, in extensive CYP2D6 metabolizers with mild hepatic impairment, no dosage adjustment (i.e., 84 mg BID) is recommended when eliglustat is administered alone, and eliglustat dosage is reduced to 84 mg QD when eliglustat is taken with a weak CYP2D6 inhibitor, or a strong, moderate, or weak CYP3A inhibitor. Eliglustat is contraindicated in extensive CYP2D6 metabolizers with moderate hepatic impairment and in extensive CYP2D6 metabolizers with mild hepatic impairment when coadministered with a strong or moderate CYP2D6 inhibitor since the mean steady state exposures were predicted much higher than the upper end of efficacious and safe exposure ranges. Eliglustat is contraindicated in patients with severe hepatic impairment due to a potential of substantially elevated plasma concentrations of eliglustat. A contraindication for eliglustat use in CYP2D6 IMs or PMs with mild and moderate hepatic impairment is proposed since the steady state exposures are unknown.

The effect of severe renal impairment was evaluated in a single dose phase 1 study described in Example 2. After a single 84 mg dose, eliglustat $C_{max}$ and AUC were similar in CYP2D6 EMs with severe renal impairment and healthy CYP2D6 EMs.

Considering the lack of effect of severe renal impairment after single doses, repeated administration of eliglustat in CYP2D6 EMs is not expected to have an impact on eliglustat exposure, since the time dependent effect due to mechanism-based inhibition of CYP2D6 is not expected to be affected by renal impairment. Therefore, no dose adjustment is proposed for CYP2D6 EMs with mild, moderate and severe RI.

Limited or no data are available in CYP2D6 EMs, IMs or PMs with end-stage renal disease and in CYP2D6 IMs or PMs with mild, moderate, or severe renal impairment; use of eliglustat in these patients should be avoided or not recommended.

What is claimed is:

1. A method of treating Gaucher disease comprising administering to a patient in need thereof an adjusted effective amount of eliglustat, or a pharmaceutically acceptable salt thereof, wherein said patient is an extensive CYP2D6 metabolizer with mild hepatic impairment and wherein said patient is concurrently taking a drug that is strong or moderate CYP3A inhibitor.

2. The method according to claim 1, wherein the adjusted effective amount is a once daily dose of 84 mg of eliglustat or a pharmaceutically acceptable salt thereof, measured in base form.

3. The method according to claim 2, wherein the eliglustat or pharmaceutically acceptable salt thereof is eliglustat hemitartrate.

4. A method of treating Gaucher disease comprising administering to a patient in need thereof an effective amount of eliglustat, or a pharmaceutically acceptable salt thereof, wherein said patient is an extensive CYP2D6 metabolizer with moderate or severe renal impairment.

5. The method according to claim 4, wherein the effective amount is a twice daily dose of 84 mg of eliglustat or a pharmaceutically acceptable salt thereof, measured in base form.

6. The method according to claim 5, wherein the eliglustat or pharmaceutically acceptable salt thereof is eliglustat hemitartrate.

7. A method for treating Gaucher disease, comprising administering an adjusted effective dose of eliglustat, or a pharmaceutically acceptable salt thereof, to a patient in need thereof in combination with a strong or moderate CYP3A inhibitor, wherein said patient is a CYP2D6 extensive metabolizer and wherein said patient has mild hepatic impairment.

8. The method according to claim 7, wherein the adjusted effect amount of eliglustat, or pharmaceutically acceptable salt thereof, is a dose of 84 mg of eliglustat, measured in base form, once daily.

9. The method according to claim 8, wherein the eliglustat or pharmaceutically acceptable salt thereof is eliglustat hemitartrate.

* * * * *